United States Patent [19]

Imblum

[11] Patent Number: 5,780,715
[45] Date of Patent: Jul. 14, 1998

[54] COMBUSTIBLE GAS MEASURING SENSOR CIRCUIT

[75] Inventor: Gregory G. Imblum, Monroeville, Pa.

[73] Assignee: Mine Safety Appliances Company, Pittsburgh, Pa.

[21] Appl. No.: 735,631

[22] Filed: Oct. 23, 1996

[51] Int. Cl.$^6$ .................................................. G01N 27/04
[52] U.S. Cl. ............................................................ 73/23.21
[58] Field of Search .............................. 73/23.31, 23.21, 73/23.32, 31.02, 31.03, 31.05; 338/34; 422/94, 95

[56] References Cited

U.S. PATENT DOCUMENTS

| | | | |
|---|---|---|---|
| 4,250,737 | 2/1981 | Biglin | 338/34 X |
| 4,538,448 | 9/1985 | Boutonnat et al. | 422/94 X |
| 4,541,988 | 9/1985 | Tozier et al. | 422/94 |
| 5,234,837 | 8/1993 | Accorsi et al. | 73/23.31 X |

*Primary Examiner*—Michael Brock
*Attorney, Agent, or Firm*—J. G. Uber; G. J. Iwanejko, Jr.

[57] ABSTRACT

The present invention relates to a programmable current or voltage sensing circuit for use in measuring concentration levels of combustible gases. Generally, the present invention provides an electrical apparatus for detecting the concentration level of a combustible gas comprising a pair of sensor elements each having an electrical output which is compared to the other for measuring the amount of the gas undergoing combustion. The apparatus also generally comprises a first pair of electrical circuits each connected to one sensor element for controlling the amount of electrical current or voltage at that element, a second electrical circuit connected to both elements for comparing the electrical outputs of the sensor elements to measure the amount of gas undergoing combustion, and a third electrical circuit having a reference output signal for individually controlling the amount of electrical current or voltage generated by each of the first electrical circuits. Preferably, the sensor elements are comprised of electrical resistors coated with a heat conducting material wherein one of the elements is further coated with a chemical substance for catalyzing combustion of the gas, such that the combustion will cause the resistance of the catalytically coated sensor element to increase relative to the resistance of the other sensor element.

20 Claims, 2 Drawing Sheets

5,780,715

1

COMBUSTIBLE GAS MEASURING SENSOR CIRCUIT

FIELD OF THE INVENTION

The present invention relates to a programmable current or voltage sensing circuit for use in measuring concentration levels of combustible gases.

BACKGROUND OF THE INVENTION

Sensors used in gas measuring instruments to detect combustible gases are typically catalytic sensors comprised of two platinum wire elements coated with alumina, with one element being coated with a chemical catalyst to serve as the detector and the second element being used as a reference element or compensator. Typically, the two elements are connected in series and powered by a current or voltage source to heat the elements to a temperature where a small amount of combustible gas will burn on the surface of the element coated with the chemical catalyst.

In prior art designs, the sensor elements form half of a Wheatstone bridge circuit. The sensor elements are matched so that in the presence of fresh air, a null voltage exists at the output of the Wheatstone bridge circuit, indicating the absence of the combustible gas. In the presence of a combustible gas such as methane, pentane or hydrogen, the chemical catalyst coating causes combustion on the surface of the detector element, which causes the temperature of the detector element to rise thus increasing its resistance. In contrast, no combustion takes place on the surface of the compensator element due to the absence of the chemical catalyst, causing its resistance to remain essentially unchanged. The increased resistance of the detector element causes an imbalance in the output of the Wheatstone bridge which is proportional to the gas concentration present at the detector element.

The present invention discloses a novel combustible gas measuring sensor circuit that is a departure from the conventional prior art Wheatstone bridge configuration. The present invention comprises a combustible gas measuring sensor circuit in which each sensor element is separately electronically controlled by a programmable current or voltage source. The current or voltage sources are ideally matched to each other such that no differential will exist between the output of the detector element and the compensator element in the absence of the combustible gas. In practice, a negligible differential will always exist due to the tolerances of the circuit components chosen. When combustion takes place on the surface of the detector element as described above, a differential between the outputs of the detector element and the compensator element will be created which is proportional and preferably linear to the amount of gas undergoing combustion.

The electronically controlled circuit of the present invention offers several advantages over the prior art Wheatstone bridge configuration. First, the power supply voltage required to run the circuit is approximately half that required for a conventional Wheatstone bridge. Second, by using separately controllable current or voltage sources, the operating characteristics of the circuit may be adjusted to account for differences in circuit components to optimize measurement performance. This permits sensing elements of different types to be used in the circuit, facilitating maintainability. Finally, different power conserving modes of operation are possible through use of the programmability features which are not possible with a conventional Wheatstone bridge. For example, each current or voltage source

2 can be operated independently of the other. In this way, both current or voltage sources can be operated simultaneously, one current source can be turned off while the other is active, or both current sources can be periodically switched on and off. This permits a conservation of operating power consumption under certain conditions.

Accordingly, the present invention provides a novel combustible gas measuring sensor circuit that is a departure from the conventional prior art Wheatstone bridge configuration.

Additionally, the present invention provides a novel combustible gas measuring sensor circuit in which each sensor element is separately electronically controlled by a programmable current or voltage source.

Additionally, the present invention provides a novel combustible gas measuring sensor circuit in which the current or voltage sources are ideally matched to each other such that a negligible differential output will exist in the absence of the combustible gas, and such that during combustion a substantial differential output will be created which is proportional to the amount of gas undergoing combustion.

Additionally, the present invention provides a novel combustible gas measuring sensor circuit in which the power supply voltage required to run the circuit is approximately half that required for a conventional Wheatstone bridge.

Additionally, the present invention provides a novel combustible gas measuring sensor circuit in which the operating characteristics of the circuit may be adjusted to account for existing tolerances in circuit components to optimize measurement performance.

Additionally, the present invention provides a novel combustible gas measuring sensor circuit which facilitates maintainability when compared to conventional combustible gas measuring sensor circuits.

Additionally, the present invention provides a novel combustible gas measuring sensor circuit which facilitates power conservation by providing differing modes of operation to reduce electrical power consumption.

SUMMARY OF THE INVENTION

Generally, the present invention provides an apparatus for detecting the concentration level of a combustible gas comprising a pair of sensor elements each having an electrical output which is compared to the other for measuring the amount of the gas undergoing combustion. The apparatus also generally comprises at least a first pair of electrical circuits each connected to one sensor element for controlling the amount of electrical current or voltage at that element, a second electrical circuit connected to both elements for comparing the electrical outputs of the sensor elements to measure the amount of gas undergoing combustion, and a third electrical circuit having a reference output signal for individually controlling the amount of electrical current or voltage generated by each of the first electrical circuits.

Preferably, the sensor elements are comprised of electrical resistors coated with a heat conducting material wherein one of the elements is further coated with a chemical substance for catalyzing combustion of the gas, such that the combustion will cause the resistance of the catalytically coated sensor element to increase relative to the resistance of the other sensor element.

The first electrical circuits are preferably comprised of an electrical semiconductor device for controlling the amount of current passing through the sensor element, along with an electrical signal processing circuit for measuring the electrical voltage across the element and for comparing the electrical voltage or current at the element to the output of the third electrical circuit to control the semiconductor device. The third electrical circuit is preferably comprised of a digital to analog conversion circuit having a preset input for conversion to the reference output signal, while the second electrical circuit is preferably comprised of an analog to digital conversion circuit which converts the electrical output of each sensor element to digital form, for input to a computer processor that compares the electrical outputs of the sensor elements to measure the amount of gas undergoing combustion. Preferably, the sensor elements and the circuit components of the electrical circuits are matched to produce an identical electrical current through each element.

The present invention also comprises a method for using the combustible gas measuring sensor circuit for detecting the concentration level of a combustible gas, preferably comprising the steps of (i) establishing a controlled amount of electrical current or voltage at each sensor element such that the difference between the electrical outputs of the elements is eliminated, (ii) exposing at least the catalytically coated element to the combustible gas and (iii) comparing the electrical outputs of the sensor elements to measure the amount of gas undergoing combustion. In this manner, the concentration levels of combustible gases such as for example, hydrogen, methane, pentane, propane, butane, hexane, and other hydrocarbons may be efficiently and accurately measured.

Other details, objects, and advantages of the present invention will become apparent in the following description of the presently preferred embodiments.

BRIEF DESCRIPTION OF THE DRAWINGS

FIGS. 1 and 1A are block circuit diagrams of the present invention.

DETAILED DESCRIPTION OF THE PREFERRED EMBODIMENTS

Figure 1:
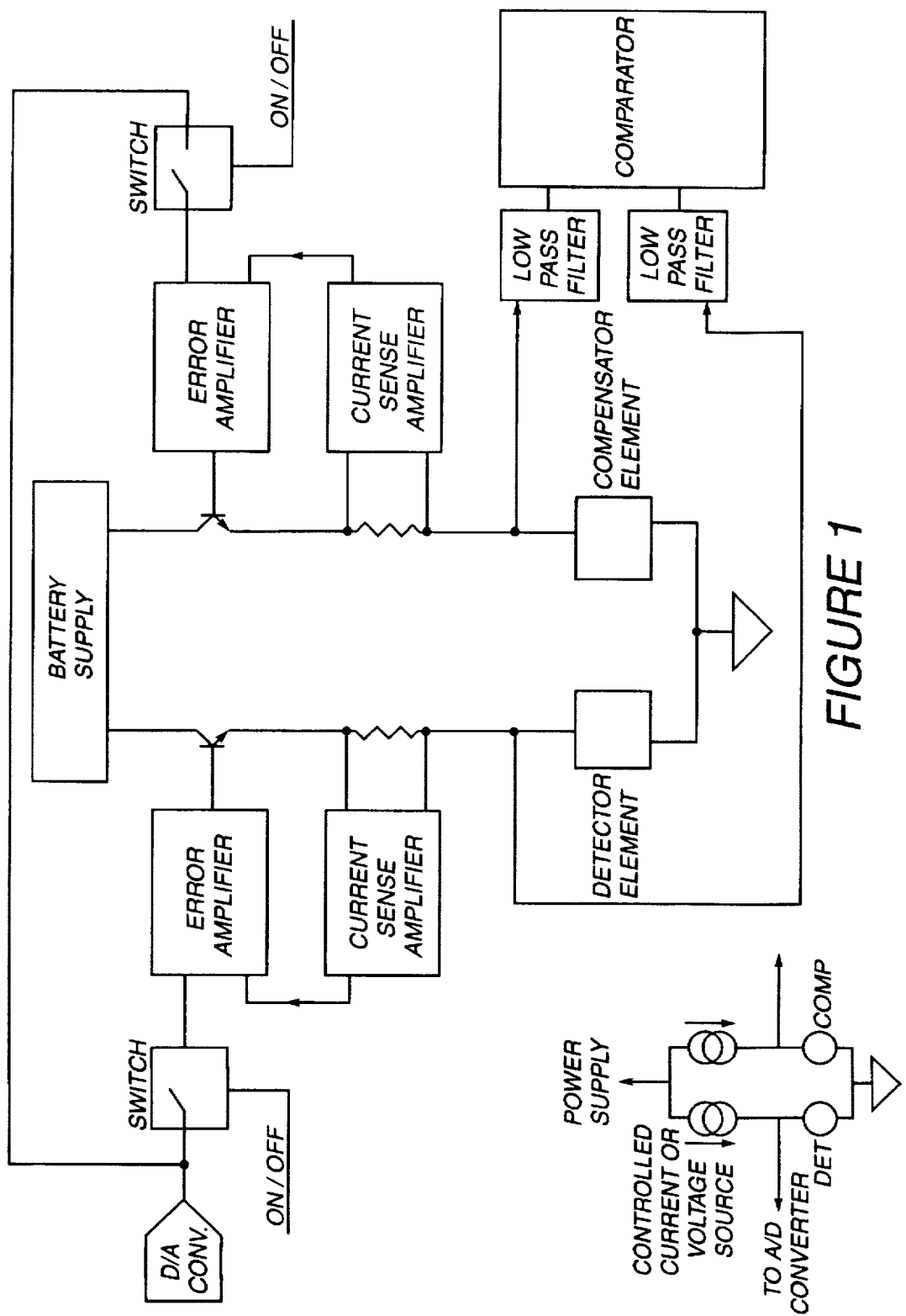
Figure 2:
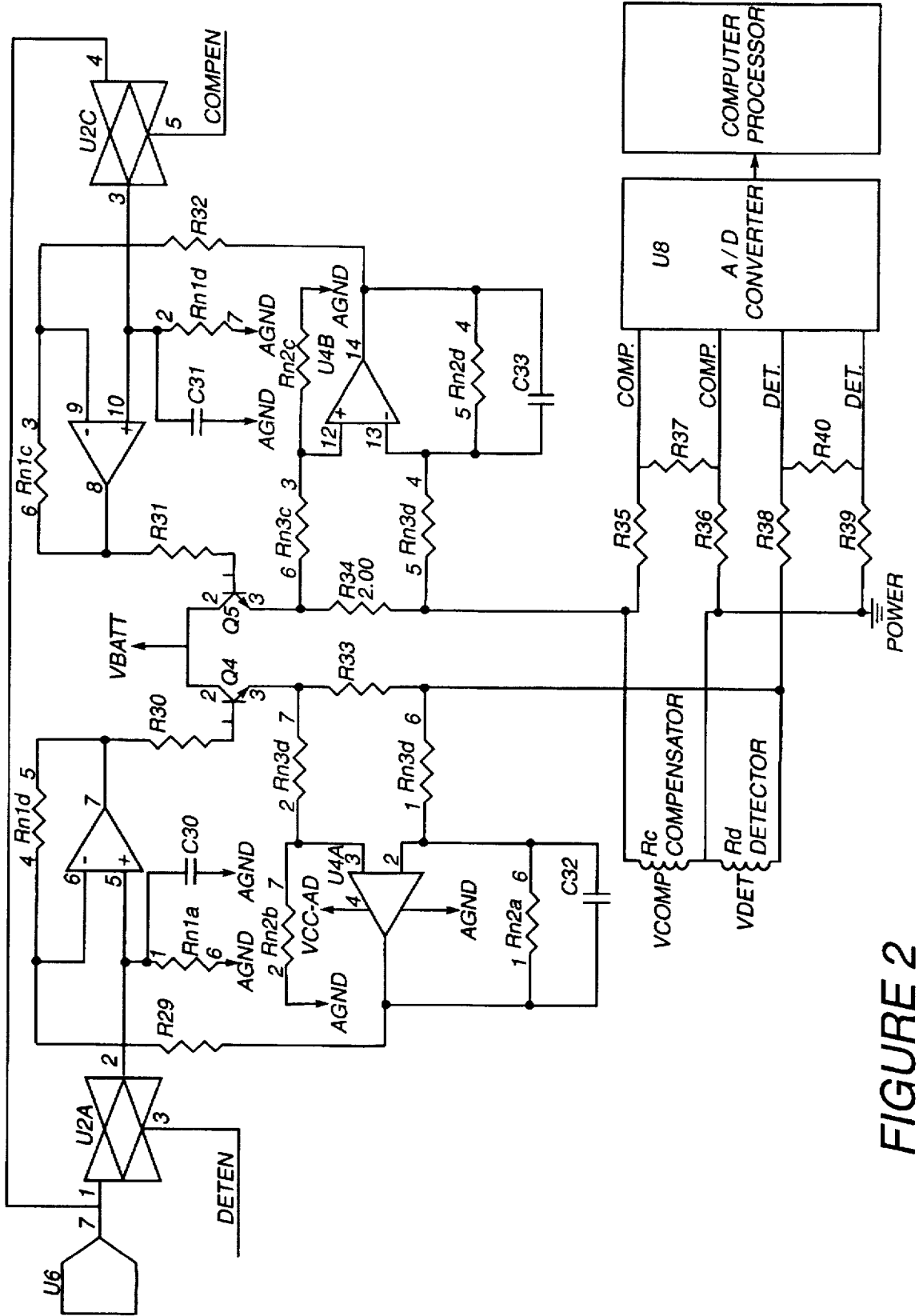
FIG. 2 is an electrical circuit diagram of a preferred embodiment of the present invention.

FIGS. 1 and 1a show the present invention in simplified block form. A preferred embodiment of the combustible gas measuring circuit is shown in FIG. 2. In this embodiment, the electronic circuit is comprised of two identical controlled current sources, enabled by transistors Q4 and Q5, respectively. Transistors Q4 and Q5 are preferably selected from the group consisting of a bipolar transistor, a junction field effect transistor, a metal-semiconductor field effect transistor, and a metal-oxide semiconductor field effect transistor. One current source Q4 passes current from the power supply Vbatt through the resistance sensor element Rd that detects the combustible gas concentration. The other current source Q5 passes current from power supply Vbatt through the reference or compensation resistance sensor element RC. Current sources Q4 and Q5 are preferably controlled by a conventional programmable digital to analog converter (DAC) U6 which sets the voltage levels at the bases of the enabling transistors Q4 and Q5 to control the amount of current flowing from the power supply Vbatt through sensor elements Rd and Rc, respectively. In the absence of the combustible gas to be detected, the current through detector element Rd is ideally regulated to equal the current through compensator element Rc. Alternately, the present invention can be arranged in a controlled voltage source configuration in which a constant identical voltage is ideally maintained across sensor elements Rd and Rc.

As shown in FIG. 2, the preferred embodiment utilizes electronic feedback circuitry to control the respective currents flowing through current sources Q4 and Q5, by comparing the voltage levels output across current sensing resisters R33 and R34, respectively, to the preprogrammed level set by DAC U6. These voltage levels are preferably measured and amplified by conventional electronic operational amplifier (op amp) differential amplifier circuits U4A and U4D, respectively. The outputs of differential amplifiers U4A and U4D are preferably passed to conventional op amp error amplifiers U4B and U4C, respectively, where they are both compared to the preprogrammed voltage level set by DAC U6. If the current through either current source Q4 or Q5 is less than the preprogrammed level set by DAC U6, the voltage output across current sensing resistors R33 or R34, as amplified by differential amplifiers U4A or U4D, respectively, will be less than the voltage level at error amplifiers U4B or U4C set by the output of DAC U6. Any differential between the output of DAC U6 and either of the current sensing resistor R33 or R34 voltage outputs will be amplified by error amplifier U4B or U4C, respectively, resulting in an increased voltage level at the base of the respective current source enabling transistor Q4 or Q5. This increased voltage level will cause transistor Q4 or Q5 to conduct more current from voltage source Vbatt through the respective current sensing resistor R33 or R34, respectively, which will in turn continue until the differential between the preprogrammed voltage level set by DAC U6 and the amplified current sensing resistor R33 or R34 output voltage disappears. At that point, the current level through current source Q4 or Q5 will equal the preprogrammed level set by DAC U6. In a constant voltage source configuration, the voltage across sensor elements Rd and RC would be compared to the value preset by DAC U6, and the current through the sensor elements Rd and Rc would ideally be adjusted to maintain a constant identical voltage across each of them, respectively. The values of the circuit components as shown in FIG. 2 are chosen so that, in the absence of a combustible gas, the current level through current source Q4 will match that through current source Q5. The comparison functions necessary for controlling current sources Q4 and Q5 can alternately be performed by means of an algorithm run on a computer processor by computer software programmed for this purpose that is stored on a computer-readable storage medium, by a digital comparison circuit, or by a combined analog and digital comparison circuit comprised of discrete electrical and digital logic components, or other similar circuitry presently in the state of the art.

The present invention measures the concentration of a selected combustible gas such as hydrogen, methane, pentane, propane, butane, hexane, and other hydrocarbons by measuring the differential output voltage Vdiff between the voltage drop Vdet across detector sensor element Rd and the voltage drop Vcomp across compensator sensor element Rc. This differential output voltage Vdiff will be directly proportional to the concentration of the detected gas. Both sensor elements Rd and Rc preferably have an identical resistance value and are preferably made of the same material, such as platinum or other electrically resistive materials known in the art. Both are also preferably coated with the same heat conducting material such as alumina or other heat conducting materials known in the art. However, detector element Rd also contains an active chemical catalyst known in the art, which will cause the combustible gas to burn on its heat conducting surface. In the presence of fresh air, since the resistances of sensor elements Rd and Rc are preferably identical, the detector element voltage drop Vdet is substantially the same as the compensator element voltage drop Vcomp, making the differential output voltage Vdiff negligible, thus indicating the absence of the detected gas. However, in the presence of the combustible gas, the resistance of detector element Rd rises due to the heating caused by the catalyst-induced combustion that takes place on its surface, which is initiated by the electrical current flowing through its heat conducting surface. In contrast, the resistance of compensator element Rc remains essentially unchanged due to a lack of combustion. This increased resistance at detector element Rd causes its voltage drop Vdet to become greater than the compensator element voltage drop Vcomp, thereby giving rise to a differential output voltage Vdiff that increases with the amount of combustion taking place, which in turn is proportional to and preferably varies linearly with the concentration of the combustible gas present at the detector element Rd. In a constant voltage source configuration, the current flowing through detector element Rd would be compared to the current flowing through compensator element Rc, and the differential output current Idiff would be proportional to the concentration of combustible gas present at detector element Rd.

Referring again to FIG. 2, sensor voltage drops Vdet and Vcomp are each preferably passed through a resistor-capacitor network C35/R38–R40 and C34/R35–R37, respectively, which attenuate and filter each signal, preferably for receipt by a conventional analog to digital (A/D) converter U8. A/D converter U8 converts the analog sensor voltage drop signals Vdet and Vcomp into digital form for comparison. Any difference between the voltage drop signals Vdet and Vcomp will give rise to a differential output voltage signal Vdiff, which can be calibrated to a known concentration level of the combustible gas present at detector element Rd to give rise to a calibration curve that can be used to measure subsequent unknown concentration levels of the combustible gas. These comparison and calibration functions can be performed by means of an algorithm run on a computer processor by computer software programmed for this purpose that is stored on a computer-readable storage medium. Other means of performing this comparison are also possible, such as use of an electronic differential amplifier circuit, an analog or a digital comparison circuit, or a combined analog and digital comparison circuit comprised of discrete electrical and digital logic components, or other similar circuitry presently in the state of the art.

Digital to analog converter U6 can be operated to independently control the current levels through current sources Q4 and Q5, through the use of analog switches U2A and U2C, in conjunction with detector element enable signal DETEN and compensator element enable signal COMPEN, respectively. By the use of enabling signals DETEN and COMPEN, analog switches U2A and U2C gate the U6 preprogrammed control voltage to error amplifiers U4B and U4C, respectively, and thus control activation of current sources Q4 and Q5, respectively. In this way, both current or voltage sources can be operated simultaneously, one current D source can be turned off while the other is active, or both current sources can be periodically switched on and off. This permits a conservation of operating power consumption under certain conditions. For example, it may be desired to operate detector element Rd continuously while at the same time switching compensator element RC on and off periodically, or vice versa. In the former case, the voltage Vdet across detector element Rd would be measured continuously while the voltage Vcomp across compensator element Rc would be periodically measured, updated and stored in computer memory. A comparison would thus be made between an instantaneously measured value for the detector voltage Vdet and a stored value for the compensator voltage Vcomp while compensator element Rc is inactive. Operating the detector element Rd continuously would be used primarily for low concentrations of the combustible gas up to the lower explosive limit (LEL) in order to continuously monitor gas concentrations as they approach the LEL. Operating the compensator element Rc continuously would be used primarily for high concentrations of the combustible gas above the LEL, where the compensator element Rc may function as a thermal conductivity element for measuring high concentrations of gases such as methane or hydrogen.

Values and models of circuit components used in a preferred embodiment of the invention shown in FIG. 2 are as follows:

TABLE 1

| | |
|---|---|
| C30 | 0.01 μF (microfarads) |
| C31 | 0.01 μF |
| C32 | 0.001 μF |
| C33 | 0.001 μF |
| C34 | 0.001 μF |
| C35 | 0.001 μF |
| Rd | 35 Ω (ohms) |
| Rc | 35 Ω |
| Rn1a | 100 kΩ (kilohms) |
| Rn1b | 100 kΩ |
| Rn1c | 100 kΩ |
| Rn1d | 100 kΩ |
| Rn2a | 100 kΩ |
| Rn2b | 100 kΩ |
| Rn2c | 100 kΩ |
| Rn2d | 100 kΩ |
| Rn3a | 10 kΩ |
| Rn3b | 10 kΩ |
| Rn3c | 10 kΩ |
| Rn3d | 10 kΩ |
| R29 | 1 kΩ |
| R30 | 100 Ω |
| R31 | 100 Ω |
| R32 | 1 kΩ |
| R33 | 2 Ω |
| R34 | 2 Ω |
| R35 | 2 kΩ |
| R36 | 2 kΩ |
| R37 | 8.06 kΩ |
| R38 | 2 kΩ |
| R39 | 2 kΩ |
| R40 | 8.06 kΩ |
| Q4 | PXT3904 (model BJT transistor) |
| Q5 | PXT3904 |
| U2A | 4066 (model analog switch) |
| U2C | 4066 |
| U4A | OP496 (model op amp) |
| U4B | OP496 |
| U4C | OP496 |
| U4D | OP496 |
| U6 | LTC1453 (model D/A converter) |
| U8 | ADD7714 (model A/D converter) |

While presently preferred embodiments of practicing the invention has been shown and described with particularity in connection with the accompanying drawings, the invention may otherwise be embodied within the scope of the following claims. The values of the circuit components shown are for illustrative purposes only, and it will be understood by those skilled in the art that the present invention can be practiced with various combinations of circuit components and is not limited to those values shown.

What is claimed is:

1. An electrical circuit for measuring the concentration level of a combustible gas comprising:
   a) a detector
   b) a compensator
   c) at least a pair of first electrical circuits, one of the pair electrically connected to the detector and the other of the pair electrically connected to the compensator, each circuit independently controlling the amount of electrical current passing through the detector or the compensator to which it is connected;

d) a second electrical circuit electrically connected to both the detector and the compensator for comparing an electrical output from each to measure the amount of combustible gas; and e) a third electrical circuit electrically connected to the pair of first electrical circuits for individually operating each first electrical circuit.

2. The circuit of claim 1, wherein the third electrical circuit comprises a pair of switches and a reference voltage generator.

3. The circuit of claim 2, wherein the reference voltage generator comprises a digital to analog conversion circuit having a preset input for creating the reference voltage.

4. The electrical circuit of claim 2, wherein each switch connects the reference voltage generator to one of the first electrical circuits such that the detector is on and the compensator is off.

5. The electrical circuit of claim 2, wherein each switch connects the reference voltage generator to one of the first electrical circuits such that the detector is off and the compensator is on.

6. The circuit of claim 1, wherein each first electrical circuit is comprised of:

a) an electrical device for varying the amount of current passing through the detector or compensator to which it is connected;

b) a first electrical signal processing circuit for measuring the amount of current passing through the detector or compensator to which it is connected; and c) a second electrical signal processing circuit having inputs connected to the first electrical signal processing circuit and to the third electrical circuit, and having an output connected to the electrical device.

7. The circuit of claim 6, wherein the electrical device is selected from the group consisting of a bipolar transistor, a junction field effect transistor, a metal-semiconductor field effect transistor, and a metal-oxide semiconductor field effect transistor.

8. The circuit of claim 6, wherein the electrical signal processing circuits are selected from the group consisting of a computer processor, an electronic differential amplifier, an electrical analog comparison circuit, an electronic digital comparison circuit and a combined analog and digital comparison circuit.

9. The circuit of claim 1, wherein the second electrical circuit is selected from the group consisting of an electronic differential amplifier, an electrical analog comparison circuit, an electronic digital comparison circuit, and a combined analog and digital comparison circuit.

10. The circuit of claim 1, wherein the second electrical circuit is comprised of:

a) an analog to digital conversion circuit with inputs electrically connected to the detector and the compensator for converting electrical signals from the detector and the compensator to digital form; and b) a computer processor connected to the analog to digital conversion circuit for comparing the signals from the detector and the compensator to measure the amount of combustible gas.

11. An electrical circuit for measuring the concentration level of a combustible gas comprising:

a) a detector
b) a compensator c) at least a pair of first electrical circuits, one of the pair electrically connected to the detector and the other of the pair electrically connected to the compensator, each circuit independently controlling the amount of electrical current passing through the detector or the compensator to which it is connected;

d) a second electrical circuit electrically connected to both the detector and the compensator for comparing an electrical output from each to measure the amount of combustible gas; and e) a third electrical circuit electrically connected to the pair of first electrical circuits that enable the first electrical circuits to be operated in more than one mode.

12. The circuit of claim 11 wherein the third electrical circuit comprises a pair of switches and a reference voltage generator.

13. The circuit of claim 12, wherein the reference voltage generator comprises a digital to analog conversion circuit having a preset input for creating the reference voltage.

14. The circuit of claim 11, wherein each first electrical circuit is comprised of:

a) an electrical device for varying the amount of current passing through the detector or compensator to which it is connected;

b) a first electrical signal processing circuit for measuring the amount of current passing through the detector or compensator to which it is connected; and c) a second electrical signal processing circuit having inputs connected to the first electrical signal processing circuit and to the third electrical circuit, and having an output connected to the electrical device.

15. The circuit of claim 14, wherein the electrical device is selected from the group consisting of a bipolar transistor, a junction field effect transistor, a metal-semiconductor field effect transistor, and a metal-oxide semiconductor field effect transistor.

16. The circuit of claim 14, wherein the electrical signal processing circuits are selected from the group consisting of a computer processor, an electronic differential amplifier, an electrical analog comparison circuit, an electronic digital comparison circuit and a combined analog and digital comparison circuit.

17. The circuit of claim 11, wherein the second electrical circuit is selected from the group consisting of an electronic differential amplifier, an electrical analog comparison circuit, an electronic digital comparison circuit, and a combined analog and digital comparison circuit.

18. The circuit of claim 11, wherein the second electrical circuit is comprised of:

a) an analog to digital conversion circuit with inputs electrically connected to the detector and the compensator for converting electrical signals from the detector and the compensator to digital form; and b) a computer processor connected to the analog to digital conversion circuit for comparing the signals from the detector and the compensator to measure the amount of combustible gas.

19. The circuit of claim 11, wherein in one mode of operation both first electrical circuits are operational and in a second mode of operation, only the electrical circuit connected to the detector is operational.

20. The circuit of claim 11, wherein in one mode of operation both first electrical circuits are operational and in a second mode of operation, only the electrical circuit connected to the compensator is operational.

* * * * *